United States Patent [19]

Nielsen et al.

[11] 4,292,297
[45] Sep. 29, 1981

[54] SELENOMETHIONINE-75SE-CONTAINING SOLUTION HAVING A THIOL AS A STABILIZER

[75] Inventors: Jan Nielsen; Karel J. Panek, both of Petten, Netherlands

[73] Assignee: Byk-Mallinckrodt Cil B.V., Petten, Netherlands

[21] Appl. No.: 11,337

[22] Filed: Feb. 12, 1979

[30] Foreign Application Priority Data

Feb. 21, 1978 [NL] Netherlands ............... 7801908

[51] Int. Cl.$^3$ .............. A61K 29/00; A61K 43/00; G01T 1/00
[52] U.S. Cl. ......................... 424/1; 128/659; 424/1.5; 424/9
[58] Field of Search ............. 424/1, 9, 1.5; 128/659

[56] References Cited

U.S. PATENT DOCUMENTS 4,083,947 4/1978 Monks et al. ................ 424/1
4,202,876 5/1980 Monks et al. ................ 424/1.5

OTHER PUBLICATIONS

Scuro et al., Chemical Abstracts, vol. 88, #13, Mar. 27, 1978, Abstract #85521k.
Blau et al., Radioactive Pharmaceuticals, AEC Symposium Series, Apr. 1966, pp. 423-428.
Risch, The Chemistry of Radiopharmaceuticals, ed. Heindel et al., Masson Publishing USA, Inc. NY, 1978, pp. 53-73.

Primary Examiner—Edward A. Miller
Assistant Examiner—Christine M. Nucker
Attorney, Agent, or Firm—Bernard, Rothwell & Brown

[57] ABSTRACT

A selenomethionine-75Se-solution, which is suitable for use as a radioactive diagnostic material in medical science applications, is stabilized with regard to maintaining its radiochemical purity by the addition of a thiol of the formula $$HS-(CH_2)_n-CHR-CO-NH-CH_2-COOH$$

in which formula n is 0 or 1 and R is a methyl group when n is 0 and a glutamyl group when n is 1.

16 Claims, No Drawings

SELENOMETHIONINE-$^{75}$SE-CONTAINING SOLUTION HAVING A THIOL AS A STABILIZER

The invention relates to a selenomethionine-$^{75}$Se-containing solution, to a method of stabilizing the solution and to a method of using said solution.

In medical science, selenomethionine-$^{75}$Se is of importance as a radiodiagnostic, for example, as a tracer for tracing tumors, in whch selenomethionine-$^{75}$Se in solution is used.

The expression, "Selenomethionine-$^{75}$Se-containing solutions" as used throughout the specification refers to solutions of selenomethionine enriched with radioactive $^{75}$Se and wherein the selenomethionine is dissolved in, or admixed with, a pharmaceutically acceptable liquid carrier. The stability of such solutions based on the radiochemical purity can be determined by the method described in the British Pharmacoporeia (1973) or by the method described in Int.J.Appl. Radiat. and Isotopes, 22, (1971) pp.569-74 by Cohen et al.

It has been found in practice, that these solutions have the disadvantage in that during storage they soon lose a part of their radiochemical purity.

However, for the utility of the solutions it is necessary that the radiochemical purity should be maintained at any rate at a level above 90%. Upon storing a selenomethionine-$^{75}$Se-containing solution, however, an unacceptable decrease of the radiochemical purity proves to occur, not only at slightly higher temperature but also already at room temperature.

It is known to stabilize a selenomethionine-$^{75}$Se-containing solution against oxidative decomposition by the addition of 2-aminoethane thiol.

For example, a product is marketed which is an aqueous solution of selenomethionine-$^{75}$Se and to which -2-aminoethane thiol has been added as an anti-oxidant.

In practice it is necessary to sterilize selenomethionine-$^{75}$Se solutions. This is usually done under the influence of heat, namely at least 20 minutes at 121° C.

It has now surprisingly been found that the radiochemical purity of a selenomethionine-$^{75}$Se-containing solution, even after sterilization at 121° C. Can be maintained for a long period of time at a level which is acceptable for practice by adding a thiol of the formula

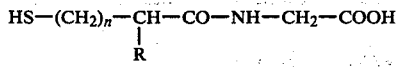

wherein n is 0 or 1, and R represents a methyl or a glutamyl group with the proviso that when n is 0, R is a methyl group, and that when n is 1, R is a glumatyl group.

The thiols according to the invention suitable for this purpose are α-mercaptopropionylglycine and glutathion.

It has been found that the stabilizing effect, that is the maintenance of the radiochemical purity of the selenomethionine-$^{75}$Se-containing solution, both of α-mercaptopropionylglycine and of glutathion is better than that of 2-aminoethane thiol.

The use of glutathion as a stabilizer has the additional advantage that this compound is an endogenous materioal. It has been found in addition that a selenomethionine-$^{75}$Se-containing solution does not discolour during the above-mentioned heat sterilisation when α-mercaptorpropionylglycine or glutathion is present as a stabilizer. This is surprising because thiols generally are very oxidation-sensitive compounds.

The good resistance of the above-mentioned thiol compounds against thermal sterilization is still emphasized by the following experiments.

Solutions of 1% of α-mercaptopropionylglycine and glutathion in water (pH 7) were heated at 121° C. for 20 minutes. Chromatography (detection with iodine vapor) yielded for both thiols only one component with the same rF value as the starting material. A more accurate method of determining this stability during thermal sterilization is the determination of the iodine consumption prior to and after sterilization. The following results were obtained with 1 ml thiol solutions:

| Thiol | quality | consumption of 0.05 N I$_2$ in ml | |
|---|---|---|---|
| | | prior to sterilization | after sterilization |
| α-mercapto-propionyl-glycine | 10 mg | 1.22 | 1.13 |
| α-mercapto-propionyl-glycine | 75 mg | 8.80 | 8.55 |
| glutathion | 117 mg | 7.05 | 6.55 |

From these results it appears that in the given conditions at most a very small oxidation of the tested thiols occurs.

The thiol to be used is added to the selenomethionine-$^{75}$Se-containing solution as such, or as a solution in water in a quantity of 0.1 to 30 mg per ml of the selenomethionine-$^{75}$Se-containing solution.

The selenomethionine-$^{75}$Se-containing solution stabilized of the invention may be used as a diagnostic without any problems even after prolonged storage under fluctuating temperatures.

It has been found that the distribution pattern of the radioactivity over the relevant organs does not differ significantly when using a stabilized selenomethionine-$^{75}$Se-containing solution as compared with an unstabilized solution. This is not obvious as such because such a quantity of thiol might easily disturb the taking up of selenomethionine-$^{75}$Se in the objective organ. Therefore the conclusion is justified that the diagnostic quality of the preparation is not adversely influenced by the addition of α-mercaptopropionylglycine or glutathion.

The invention will now be described in greater detail with reference to the following specific examples.

EXAMPLE 1

The equimolar quantities of thiol stated in the table below were added to a solution of 100 mg of selenomethionine-$^{75}$Se, obtained as described in the Applicants' British Pat. No. 1,281,293, in 1200ml of physiological salt solution having a radiation activity of 600 millicuries. The variation of the radiochemical purity of these solutions after sterilization at 121° C. was determined after storage at 22° C.

The results are recorded in the table below. The recorded numbers are the arithmetical average of each time 2 values determined by means of a paperchromatographic analysis method described in British Pharmacopoeia 1973.

| Stabilizer | quality (in mg/ml) | radiochemical purity in % after storage (days) | | | |
|---|---|---|---|---|---|
| | | 0 | 17 | 40 | 121 |
| α-mercapto-propionyl-glycine | 9 | 97.0 | 94.9 | 95.6 | 93.1 |
| 2-aminoethane-thiol (known) | 6 | 97.7 | 90.0 | 87.9 | 88.7 |
| None (control) | — | 96.1 | 74.5 | 76.4 | 63.0 |

EXAMPLE 2

In a corresponding manner as in Example 1, the stability of selenomethionine-$^{75}$Se-containing solutions was determined at 20° and 50° C. Besides by means of the method from British Pharmaceopoeia (B.P.) stated in example 1 the radiochemical purity was also determined according to Cohen, et al, Int. J. Appl. Radiat. and Isotopes 22, (1971), 569–74.

| stabilizer | content per 0.5 mCI (in mg/ml) | radiochemical purity in % after days storage at 50° C. | | | |
|---|---|---|---|---|---|
| | | 0 | | 47 | |
| | | B.P. | Cohen | B.P. | Cohen |
| — | 0 | 97.6 | 97.2 | 86.0 | 83.9 |
| α-mercapto-propionyl-glycine | 3 | 97.3 | 96.8 | 94.8 | 95.0 |
| α-mercapto-propionyl-glycine | 9 | 98.1 | 98.2 | 95.9 | 97.0 |
| α-mercapto-propionyl-glycine | 27 | 98.0 | 98.4 | 96.3 | 96.2 |
| glutathion | 5 | 97.7 | 97.9 | 93.3 | 95.2 |
| glutathion | 10 | 98.4 | 98.5 | 93.4 | 96.1 |
| glutathion | 20 | 98.3 | 98.5 | 94.6 | 94.9 |

| stabilizer | content per 0.5 mCi (in mg/ml) | radiochemical purity in % after days storage at 20° C. | | | | | |
|---|---|---|---|---|---|---|---|
| | | 0 | | 35 | | 141 | |
| | | B.P. | Cohen | B.P. | Cohen | B.P. | Cohen |
| — | 0 | 95.5 | 98.4 | 84.3 | 86.0 | 61.5 | 35.3 |
| α-mercapto-propionyl-glycine | 3 | 95.4 | 95.7 | 94.0 | 93.8 | 93.5 | 92.9 |
| α-mercapto-propionyl-glycine | 9 | 97.3 | 97.4 | 94.6 | 95.2 | 91.8 | 94.5 |
| α-mercapto-propionyl-glycine | 27 | 96.8 | 96.9 | 93.4 | 95.0 | 92.6 | 94.6 |
| glutathion | 5 | 97.4 | 97.1 | 95.0 | 92.1 | 90.4 | 93.6 |
| glutathion | 20 | 97.1 | 97.6 | 95.9 | 94.5 | 95.1 | 91.3 |
| glutathion | 80 | 97.4 | 98.4 | 94.1 | 94.2 | 96.2 | 91.4 |

EXAMPLE 3

Investigation into the distribution pattern of the radioactivity over the relevant organs with a selenomethionine-$^{75}$-Se-containing solution stabilized with α-mercaptopropionylglycine.

Guinea pigs were divided into groups of 4 experimental animals. A quantity of selenomethionine-$^{75}$Se- in solution corresponding to a dose usual for human administration of approximately 4 µCi per kg of body weight was administered intravenously to all experimental animals). 1, 2, 6 and 24 hours, respectively, after the injection, the relevant organs of each time 1 group of experimental animals were removed. The radioactivity of these organs was measured by means of a Packard autogammaspectrometer. The results obtained were used to calculate for each of the removed organs the percentage of the injected dose of selenomethionine-$^{75}$Se per gram of organ weight. For comparison the same experiment was carried out in which experimental animals were injected with an unstabilized selenomethionine-$^{75}$Se solution. The results are recorded in the table below; the numbers are provided with the calculated standard deviations.

Percentage of selenomethionine-$^{75}$Se per gram of organ weight.

Time interval between injection and removal of the organs.

| Organs/tissues | time interval of 1 hours | |
|---|---|---|
| | A | B |
| pancreas | 1.93 ± 0.74 | 2.02 ± 0.63 |
| liver | 1.32 ± 0.06 | 1.37 ± 0.07 |
| gall-bladder + contents | 0.38 ± 0.23 | 0.37 ± 0.23 |
| small intestines | 0.68 ± 0.31 | 0.76 ± 0.12 |
| caecum | 0.15 ± 0.04 | 0.17 ± 0.01 |
| large intestines | 0.23 ± 0.06 | 0.24 ± 0.04 |
| blood | 0.11 ± 0.00 | 0.12 ± 0.02 |
| kidneys | 0.83 ± 0.07 | 0.87 ± 0.16 |
| muscle tissue | 0.18 ± 0.01 | /.16 ± 0.03 |

A = selenomethionine-$^{75}$Se.
B = selenomethionine-$^{75}$Se., stabilized with x-mercaptopropionylglycine.

| organs/tissues | time interval of 2 hours | |
|---|---|---|
| | A | B |
| pancreas | 1.85 ± 0.28 | 2.07 ± 0.48 |
| liver | 1.43 ± 0.33 | 1.41 ± 0.09 |
| gall-bladder + contents | 0.42 ± 0.15 | 0.39 ± 0.02 |
| small intestines | 1.02 ± 0.16 | 1.00 ± 0.17 |
| caecum | 0.27 ± 0.03 | 0.25 ± 0.04 |
| large intestines | 0.37 ± 0.04 | 0.34 ± 0.05 |
| blood | 0.17 ± 0.02 | 0.17 ± 0.01 |
| kidneys | 1.19 ± 0.09 | 1.16 ± 0.04 |
| muscle tissue | 0.17 ± 0.01 | 0.18 ± 0.04 |

| organs/tissues | time interval of 6 hours | |
|---|---|---|
| | A | B |
| pancreas | 1.60 ± 0.44 | 1.21 ± 0.40 |
| liver | 0.92 ± 0.12 | 0.94 ± 0.19 |
| gall-bladder + contents | 0.34 ± 0.22 | 0.27 ± 0.15 |
| small intestines | 0.72 ± 0.06 | 0.85 ± 0.15 |
| caecum | 0.20 ± 0.04 | 0.19 ± 0.03 |
| large intestines | 0.33 ± 0.03 | 0.34 ± 0.10 |
| blood | 0.25 ± 0.03 | 0.25 ± 0.04 |
| kidneys | 1.21 ± 0.10 | 1.16 ± 0.16 |
| muscle tissue | 0.15 ± 0.02 | 0.16 ± 0.05 |

| organs/tissues | time interval of 24 hours | |
|---|---|---|
| | A | B |
| pancreas | 0.80 ± 0.14 | 0.67 ± 0.06 |
| liver | 0.95 ± 0.08 | 0.96 ± 0.09 |
| gall-bladder + contents | 0.16 ± 0.04 | 0.19 ± 0.08 |
| small intestines | 0.53 ± 0.05 | 0.49 ± 0.05 |
| caecum | 0.23 ± 0.03 | 0.23 ± 0.04 |
| large intestines | 0.28 ± 0.03 | 0.27 ± 0.03 |
| blood | 0.21 ± 0.03 | 0.17 ± 0.01 |
| kidneys | 1.05 ± 0.06 | 0.98 ± 0.09 |
| muscle tissue | 0.14 ± 0.02 | 0.18 ± 0.01 |

The above series of numbers A and B do not differ significantly, so that the conclusion may be drawn, that the addition of α-mercaptopropionylglycine to a solution of selenomethionine-$^{75}$Se does not influence the distribution pattern over the various examined organs.

What is claimed is:

1. A stabilized selenomethionine solution for use as radiodiagnostic material in the medical sciences, comprising selenomethionine enriched with radioactive $^{75}$Se, and a thiol dissolved in a pharmaceutically acceptable liquid carrier, the thiol being an organic compound as represented by the formula $$HS-(CH_2)_n-CHR-CO-NH-CH_2-COOH$$

in which formula n is 0 or 1 and R is a methyl group or a glutamyl group with the proviso that when n is 0, R represents the methyl group and when n is 1, R represents the glutamyl group.

2. A solution as claimed in claim 1, sterilized by heating for at least 20 minutes at a temperature of 121° C.

3. A solution as claimed in claim 1 or 2, wherein the solution contains the thiol in a quantity of 0.1 to 30 mg per ml of solution.

4. A solution as claimed in claim 1 or 2, wherein the solution contains α-mercaptopropionylglycine as the thiol.

5. A solution as claimed in claim 1 or 2, wherein the solution contains glutathion as the thiol.

6. A method of stabilizing a selenomethionine solution comprising selenomethionine enriched with radioactive $^{75}$Se dissolved in a pharmaceutically acceptable liquid carrier comprising incorporating into the solution a thiol as represented by the formula $$HS-(CH_2)_n-CHR-CO-NH-CH_2-COOH$$

in which formula n is 0 or 1 and R is a methyl group or a glutamyl group with the proviso that when n is 0, R represents the methyl group and when n is 1, R represents the glutamyl group.

7. A method of stabilizing a selenomethionine solution as claimed in claim 6 wherein the thiol is incorporated into the solution prior to sterilization and in the quantity of 0.1 to 30 mg per ml of solution.

8. A method of performing radiodiagnostic tests comprising administering to an animal a stabilized selenomethionine solution comprising selenomethionine enriched with radioactive $^{75}$Se and a thiol dissolved in a pharmaceutically acceptable liquid carrier, the thiol being an organic compound as represented by the formula $$HS-(CH_2)_n-CHR-CO-NH-CH_2-COOH$$

in which formula n is 0 or 1 and R is a methyl group or a glutamyl group with the proviso that when n is 0, R represents the methyl group and when n is 1, R represents the glutamyl group.

9. A solution as claimed in claim 3 wherein the solution contains α-mercaptopropionylglycine as the thiol.

10. A solution as claimed in claim 3 wherein the solution contains glutathion as the thiol.

11. A method as claimed in claim 8 wherein the solution is sterilized by heating for at least 20 minutes at a temperature of 121° C. prior to administration.

12. A method as claimed in claim 8 or 11 wherein the solution contains the thiol in a quantity of 0.1 to 30 mg per ml of solution.

13. A method as claimed in claim 8 or 11, wherein the solution contains α-mercaptopropionylglycine as the thiol.

14. A method as claimed in claim 8 or 11, wherein the solution contains glutathion as the thiol.

15. A method as claimed in claim 12, wherein the solution contains α-mercaptopropionylglycine as the thiol.

16. A method as claimed in claim 12, wherein the solution contains glutathion as the thiol.

* * * * *